United States Patent [19]

Thompson

[11] Patent Number: 5,448,177

[45] Date of Patent: Sep. 5, 1995

[54] APPARATUS FOR MONITORING THE INTEGRITY OF A PERSONAL PROTECTIVE BARRIER

[76] Inventor: Robert L. Thompson, 9506 Heathdale Dr., Dallas, Tex. 75243

[21] Appl. No.: 101,484

[22] Filed: Aug. 2, 1993

[51] Int. Cl.⁶ .......................................... G01R 31/12
[52] U.S. Cl. .................................. 324/557; 324/693; 324/556; 340/540; 606/34; 73/45.5
[58] Field of Search .............. 324/555, 556, 557, 693, 324/694; 340/540, 605, 647; 73/40, 45.5; 2/159, 167, 168; 606/34

[56] References Cited

U.S. PATENT DOCUMENTS

| 2,981,886 | 4/1961 | Beck | 324/557 |
|---|---|---|---|
| 3,912,879 | 10/1975 | Lawson | 324/556 X |
| 4,206,632 | 6/1980 | Nysse et al. | 73/40 |
| 4,321,925 | 3/1982 | Hoborn et al. | 606/34 |
| 4,799,384 | 1/1989 | Casali | 73/45.5 |
| 4,909,069 | 3/1990 | Albin et al. | 324/557 X |
| 4,956,635 | 9/1990 | Langdon | 340/540 |
| 5,196,799 | 3/1993 | Beard et al. | 324/557 |
| 5,204,632 | 4/1993 | Leach | 324/557 |
| 5,351,008 | 9/1994 | Leach et al. | 324/556 X |

FOREIGN PATENT DOCUMENTS

| 2208300 | 6/1974 | France . |
| 0712082 | 1/1980 | U.S.S.R. . |

*Primary Examiner*—Kenneth A. Wieder
*Assistant Examiner*—Diep Do
*Attorney, Agent, or Firm*—John M. Cone; William L. Clayborn

[57] ABSTRACT

A method and apparatus for detecting the possibility of transfer of material through a protective barrier between a worker and an external object and warning the worker of that possibility is provided. In one embodiment, an electronic leak alarm module is electrically connected to the worker and to the external object. In another embodiment, the module is connected to the worker and a conductive layer on or within the protective barrier.

3 Claims, 6 Drawing Sheets

APPARATUS FOR MONITORING THE INTEGRITY OF A PERSONAL PROTECTIVE BARRIER

BACKGROUND OF THE INVENTION

The present invention relates generally to protective barriers, such as gloves and clothing, used by health care providers and others exposed to hazardous liquids. More specifically, the invention relates to an improved personal protective barrier system for warning a worker when a failure of a protective barrier occurs or is imminent.

The possibility of contact between workers and hazardous liquids is a widespread problem. In the health care industry, for example, contact between a health care provider and a patient presents the possibility of transmission of liquid-borne pathogens from the patient to the worker and vice versa. To prevent such contact with hazardous liquids, health care workers commonly wear protective barriers such as protective clothing, gloves, masks, etc.

Latex gloves are commonly used as protective barriers in the health care industry. In use, the protective barrier provided by such gloves frequently fails to perforation or tearing. In addition, when exposed to liquid, such gloves eventually become saturated with the liquid, thereby providing a path along which pathogens can be communicated from the worker to the patient and vice versa. Unfortunately, a failure of the protective barrier due to liquid saturation is not discernable by the worker.

It is known that the electrical resistance of a latex glove decreases as it becomes saturated with liquid, the resistance of the glove being inversely proportional to the degree of saturation. Thus, the glove's efficacy as a protective barrier may be tested using electrical means.

U.S. Pat. No. 4,321,925 (Hoborn) discloses a device which is electrically connected to a patient and to a health care provider, i.e., a doctor. When the electrical resistance between the doctor and patient decreases below a predetermined value, indicating a failure of a protective barrier between the doctor and patient, an alarm is sounded.

U.S. Pat. No. 4,956,635 (Langdon) discloses an improvement to the Hoborn device. In addition to providing an alarm when the electrical resistance between the health care provider and patient decreases below a predetermined value, the Langdon device provides a visual status signal for verifying that the provider is electrically connected to the device. To ensure that the device will sound an alarm when the protective barrier fails, the provider must monitor the visual status signal frequently. Unfortunately, the provider, intent on his or her work, may fail to monitor the visual status signal adequately and, thus, be unaware that the device is not functioning due to loss of electrical contact with provider. In addition, electrical power for the device is supplied by a battery, and the device provides no indication of the battery's state of charge. Should the battery become discharged while the device is being used, the provider will be unaware that the device will not function.

SUMMARY OF THE INVENTION

An object of the present invention is to provide a reliable, convenient, and cost-effective device for warning a worker of the failure or imminent failure of a personal protective barrier.

In one embodiment of the invention, a leak alarm module is electrically connected to a surgeon and to a patient. If a transfer of liquid-borne pathogens through the surgeon's gloves is possible, the module provides a warning to the surgeon tactiley and visually. In another embodiment of the invention, the electrical connection between the alarm module and the patient is not necessary. Rather, the module is connected to a conductive layer of the surgeon's gloves and/or other protective garments.

DETAILED DESCRIPTION

Figure 1:
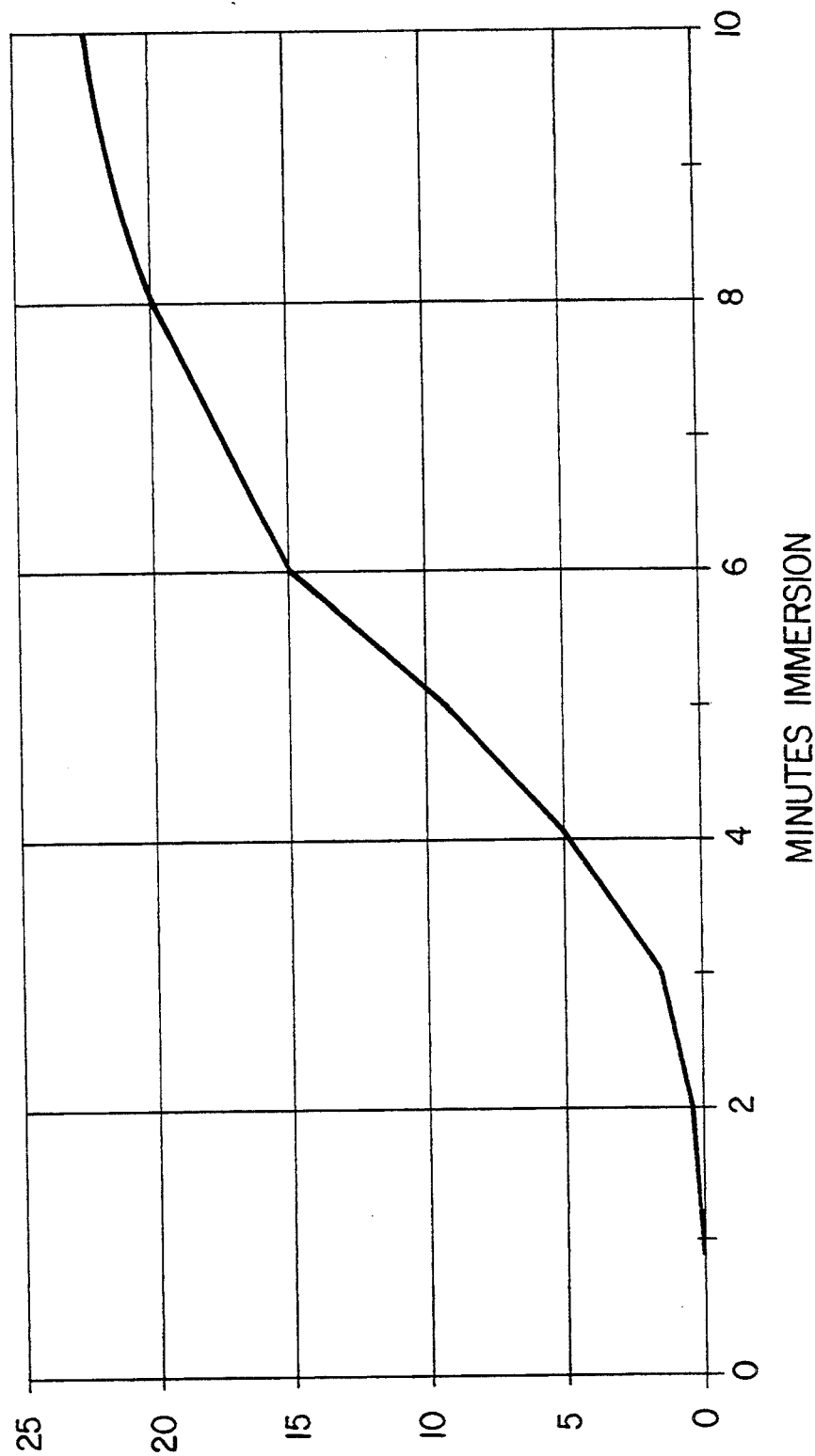
FIG. 1 is a graph which illustrates the effect of immersing a latex glove in a saline solution.

FIG. 1 shows the results of a conductivity test performed on a new latex glove. The glove was placed in a series circuit with a 2.8 v battery and a resistance of 120 KΩ. The glove was then immersed in a saline solution and the current in the circuit was measured at one minute intervals. As can be seen, initially the current in the circuit was negligible, indicating that the glove was an effective protective barrier. Thus, initially, the glove's resistance was very high, i.e., greater than 10 MΩ. At 2 minutes, the glove's resistance had decreased to 6.7 MΩ. The glove's resistance continued to decrease until, after 10 minutes, its resistance was 15 KΩ. A similar test was performed on a new glove which had a been punctured with a small needle. The initial resistance of the punctured glove was 75 KΩ, which is equal to the resistance of an unpunctured glove after six minutes of immersion.

While the described test exposed the gloves to more rigorous liquid saturation conditions than those generally encountered in the operating environment, the test illustrates the relatively rapid decrease in the efficiency of a glove as a protective barrier due to immersion in liquids.

Figure 2:
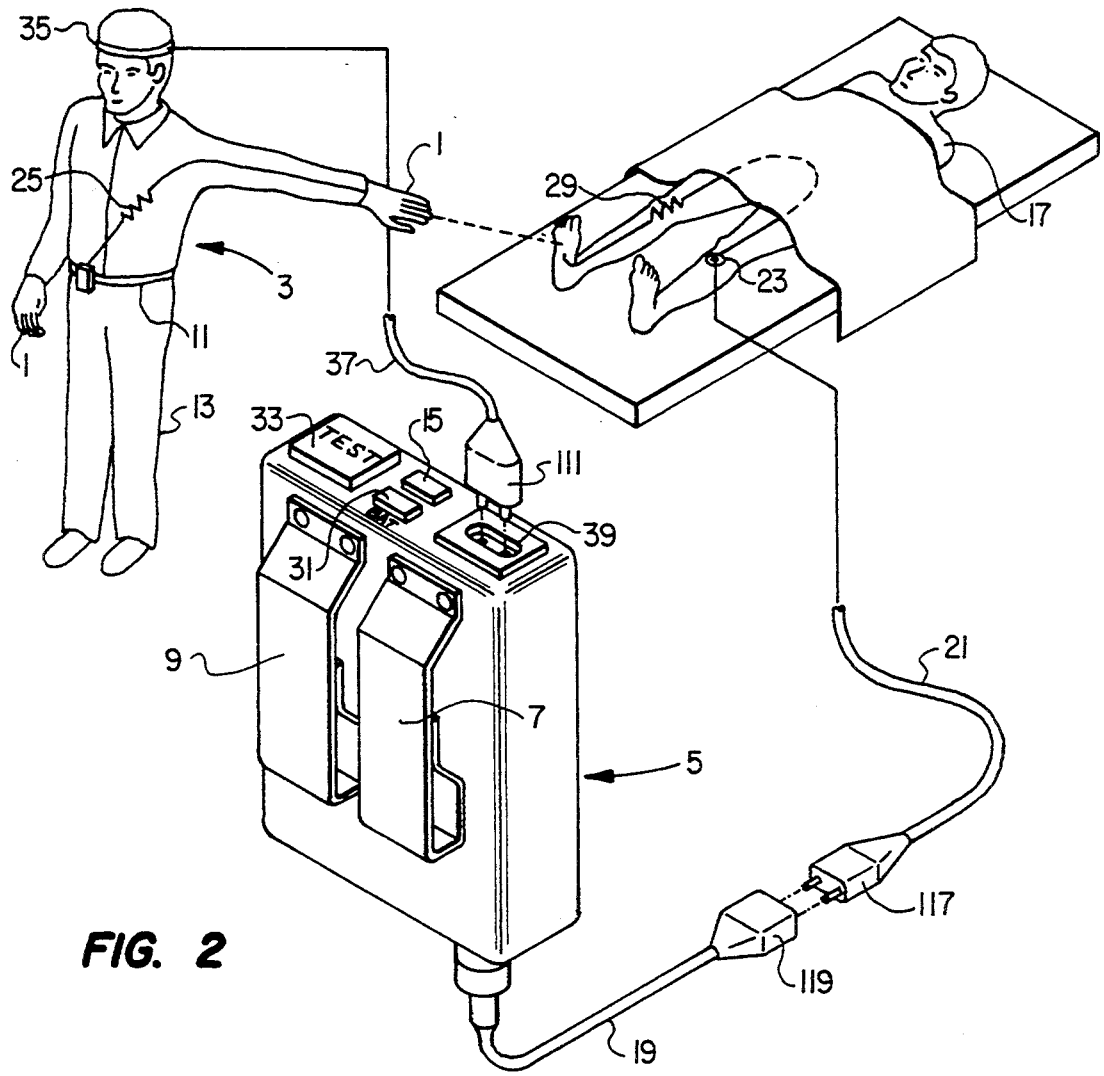
FIG. 2 illustrates an embodiment of the present invention which is configured to detect leaks in the gloves of a surgeon.
Figure 3:
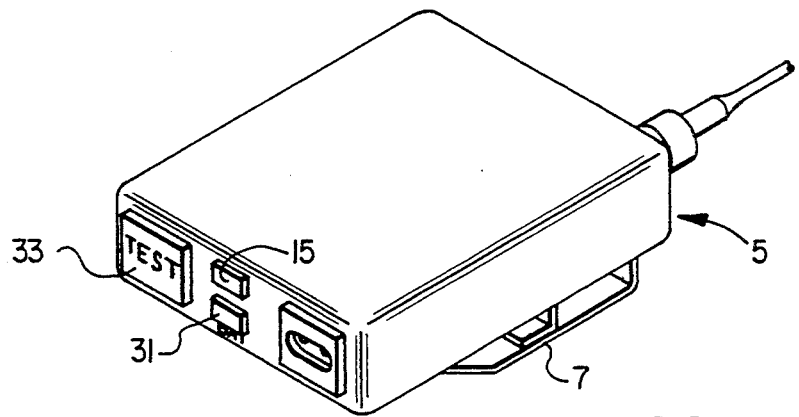
FIG. 3 is an enlarged view of the leak alarm module shown in FIG. 2.

FIGS. 2 and 3 illustrate an embodiment of the invention which is configured to detect leaks in the gloves 1 of a surgeon 3 or other operating room worker. A small, easily portable leak alarm module 5 includes two belt clips 7, 9 which are mechanically attached to the alarm module 5 and electrically connected to electronic circuits contained therein. The circuits will be described in connection with FIG. 4. The alarm module 5 is worn in a convenient location on the waistband 11 of a surgeon's (or other operating room worker's) "scrub trousers" 13. The clips are positioned so that they are in contact with the surgeon's skin. A vibrator within the module 5 and an alarm light-emitting diode ("LED") 15 provide tactile and visual warnings, respectively, (a "continuity alarm") to alert the surgeon 3 if one or both of the belt clips 7, 9 lose contact with the surgeon's skin.

The module 5 is electrically connected to a patient 17 by means of a module lanyard 19, a patient lanyard 21, and an EKG-type patient contact 23. When the surgeon 3 touches the patient 17 with either of his or her gloved hands, a series circuit external to the alarm module 5 is established between belt clip 9 and the module lanyard 19. The external circuit's resistance is comprised of the surgeon's electrical resistance 25, the glove's resistance 27 (not shown in FIG. 2), and the patient's electrical resistance 29; however, the glove's resistance 27 has the greatest effect on the current which flows in the circuit. When the glove 1 is new, that is, when it is providing an effective protective barrier between the surgeon 3 and the patient 17, its resistance 27 is very high, and little or no current will flow in the circuit. If the glove 1 is torn or punctured, its resistance 27 decreases markedly, thereby allowing the current in the circuit to increase. When the current increases to a predetermined level, the module's vibrator 59 (FIG. 4) and alarm LED 15 provide tactile and visual warnings, respectively, (a "glove failure alarm") to alert the surgeon 5 of the glove's failure. When, as a result of partial saturation due to contact with liquids (such as the surgeon's perspiration, the patient's bodily fluids, or irrigation solutions), the glove's resistance decreases, allowing the current in the circuit to increase to a predetermined level, the vibrator 59 and alarm LED 15 provide visual and tactile warnings, respectively, indicating that glove failure is imminent (an "imminent failure alarm"). As the glove 1 becomes saturated to the point where it is not effective as a protective barrier, the imminent failure alarm changes to a glove failure alarm.

A battery within the module 5 provides power for the module 5 and for the external belt clip-surgeon-patient circuit. A status indicator 31 provides a visual indication if the battery voltage is low, allowing the battery to be changed well before the module 5 fails to function due to insufficient energy remaining in the battery.

A test button 33 allows the module's circuits and the battery condition to be tested by the surgeon 3.

Rather than the belt clips 7, 9, a conductive headband 35 and a corresponding lanyard 37 may be used to provide electrical contact between the surgeon 3 and the module 5. Alternately, a conductive belt (not shown) or EKG-type contacts (not shown) could provide the connection. In any event, the electrical connection to the module 5 is made at an alternate skin contact connector 39.

Figure 4:
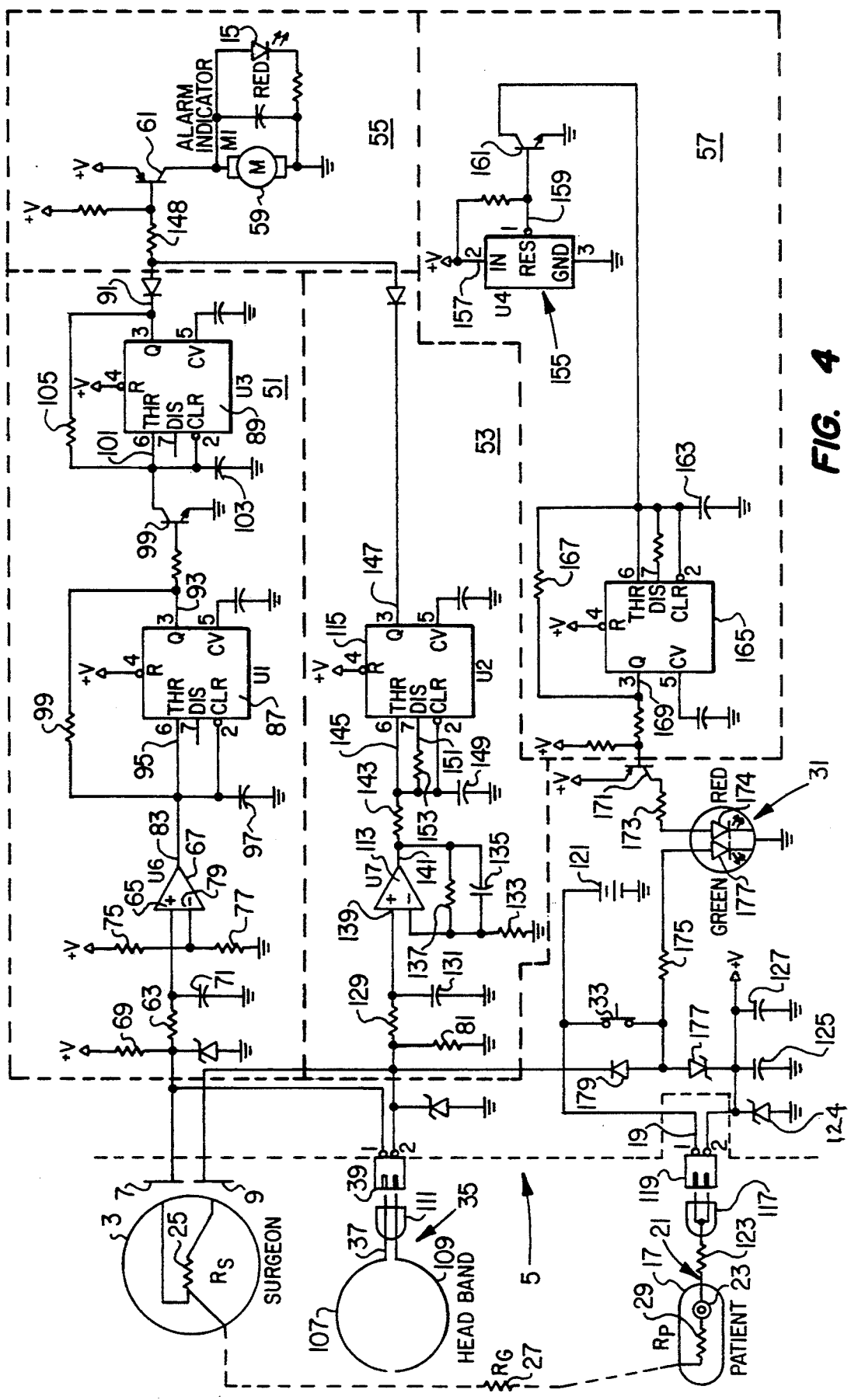
FIG. 4 is a schematic diagram of the circuitry of the leak alarm module shown in FIGS. 2 and 3.

Referring now to FIG. 4, the module's circuits comprise a continuity sensing circuit 51, a leak detector circuit 53, and alarm indicator 55, and a low voltage detection circuit 57.

THE ALARM INDICATOR

The alarm indicator 55 includes the vibrator 59, the alarm LED 15, and a transistor 61. Battery voltage, +V, is applied to the emitter of the transistor 61. When a LOW signal is applied to the transistor's base, the transistor 61 is forward biased, which applies +V to the vibrator 59 and the LED 15, causing the vibrator 59 to vibrate and the LED 15 to illuminate. When a HIGH signal is applied to the transistor's base, the transistor 61 is cut off, and no power is applied to the vibrator 59 and LED 15.

A vibrator 59 was selected as the primary alarm means for this embodiment, because aural alarm means, such as beepers, can be distracting or not be heard over the background noise of the operating room. If desired, an aural alarm means may easily be substituted for, or provided in addition to, the vibrator 59.

THE CONTINUITY CIRCUIT

The continuity circuit 51 controls the alarm indicator 55 to warn the surgeon 3 when the surgeon's skin is not contacted by the belt clips 7, 9. One belt clip 7 is connected through a resistor 63 to the positive input 65 of a comparator 67. Battery voltage is applied to the comparator input circuit through resistor 69. Resistor 63 and capacitor 71 form a low-pass filter which, together with zener diode 73, prevents voltage transients from affecting the operation of the comparator 67. A voltage divider consisting of resistors 75 and 77 apply a reference voltage to the negative input 79 of the comparator 67. It will be appreciated that the reference voltage is less than +V.

When the belt clips 7, 9 are in contact with the surgeon's skin, a circuit is established from +V through resistor 69, to the belt clip 7, through the surgeon's electrical resistance 25, to belt clip 9, and through resistor 81 to ground. In this embodiment, the values of the resistors in the circuit are: resistor 69, 10MΩ; resistor 25, 10–20KΩ (typically); and resistor 81, 100KΩ. Due to the relative values of the resistors 69, 25, 81 in the circuit, the voltage applied to the positive input 65 of the comparator 67 is essentially at ground. Because the voltage at the positive input 65 of the comparator 67 is less than that at the negative input 79, the output 83 of the comparator 67 is held LOW, essentially at ground potential. When one or both of the belt clips 7, 9 is not in contact with the surgeon's skin, the voltage applied to the positive input 65 of the comparator 67 will rise to +V. As a result, the positive input 67 becomes greater than the negative input 79, and the output 83 of the comparator 67 becomes HIGH, essentially +V.

The output 83 of the comparator 67 controls the operation of two 555-type timers 87, 89. The timers 87, 89 are configured as astable multivibrators, and act together to generate a double-pulse output 89 which controls the alarm indicator 55.

The first timer 87 has an output period of eight seconds: four seconds HIGH, four seconds LOW. When the comparator output 83 is LOW (i.e., when the belt clips 7, 9 are in contact with the surgeon's skin), the input 95 of the first timer 87 is held LOW, which holds the timer output 93 HIGH. When the comparator output 83 rises HIGH due to a break in skin contact, capacitor 97 is allowed to charge through resistor 99. When the voltage across capacitor 97 reaches the upper threshold voltage of the first timer 87, the timer output 93 switches to LOW, which causes capacitor 97 to discharge through resistor 99. When the voltage across capacitor 97 reaches the lower threshold voltage of the first timer 87, the timer output 93 switches to HIGH. The output period of the first timer 87 is controlled by its upper and lower threshold voltages, capacitor 97, and resistor 99.

The second timer 89 has an output period of two seconds: one second HIGH, one second LOW. When the output 93 of the first timer 87 is HIGH (i.e., the belt clips 7, 9 are in contact with the surgeon's skin, or one or both of the clips 7, 9 is not in contact with the surgeon's skin and the first timer 87 is in the 4-second LOW portion of its output period), transistor 99 is forward-biased, and the input 101 of the second timer 89 is held at ground potential. As a result, the output 91 of the second timer 89 is held HIGH. When the output 93 of the first timer 87 is LOW (i.e., when one or both of the belt clips 7, 9 are not in contact with the surgeon's skin and the first timer 87 is in the HIGH portion of its output period), transistor 99 is cutoff, and capacitor 103 charges through resistor 105. When the voltage across capacitor 103 reaches the upper threshold voltage of the second timer 89, the output 91 of the timer 89 switches to LOW, which causes capacitor 103 to discharge through resistor 105. When the voltage across capacitor 103 reaches the lower threshold voltage of the second timer 89, the output 91 of the timer 89 switches to HIGH.

The output 91 of the second timer 89 controls the alarm indicator 55. When the second timer output 91 is HIGH, transistor 61 is cut off, and no power is applied to the vibrator 59 and the alarm LED 15. When the output 91 of the second timer 89 is LOW, transistor 61 is biased on, and +V is applied to the vibrator 59 and the alarm LED 15, causing the vibrator 59 to vibrate and the alarm LED 15 to illuminate. It will be appreciated that so long as the belt clips 7, 9 are in contact with the surgeon's skin, the continuity circuit 51 will not cause the alarm indicator 55 to operate. When one or both of the belt clips 7, 9 is not in contact with the surgeon's skin, the continuity circuit 51 causes the alarm indicator 55 to produce the tactile and visual continuity alarm, which has the following pattern: one second on, one second off, one second on, five seconds off, repeat. The continuity alarm is readily distinguishable from the glove failure and imminent glove failure alarms (discussed below), which allows the surgeon 3 to correct the problem causing the alarm without difficulty; i.e., to place the belt clips 7, 9 in contact with his or her skin.

As mentioned above, alternate means may be used to contact the surgeon's skin. For example, the headband 35 shown comprises two conductive elements 107, 109, a dual-conductor lanyard 37, and a connector 111. When the headband's conductive elements 107,109 are in contact with the surgeon's skin and the connector 111 is plugged into the module's alternate skin contact connector 39, the conductive elements 107,109 accomplish the same function as that described above in connection with the belt clips 7, 9.

THE LEAKAGE DETECTOR CIRCUIT

The leakage detector circuit 53, which also controls the alarm indicator 55, comprises an amplifier 113 and a 555-type timer 115. When a patient lanyard connector 117 is plugged into a module lanyard connector 119, voltage is supplied from the battery 121, through the module lanyard connector 119, the patient lanyard connector 117, and the patient lanyard 21 to the patient contact 23. A resistor 123 in the patient lanyard 21 acts to limit current if the patient contact 23 and the belt clip 9 are shorted together.

It will be observed that the pins of the patient lanyard connector 117 are shorted together. When the connector 117 is plugged into the module lanyard connector 119, the battery 121 is connected to supply +V power to the remainder of the module's circuits. Thus, the patient lanyard connector 117 functions as an on-off switch for the module 5. Zener diode 124 and capacitors 125, 127 act to isolate the module's circuits from any voltage transients which may be introduced from patient lanyard 21.

Resistor 129 and capacitor 131 and resistor 137 and capacitor 135 form low-pass filters to eliminate the effect on the amplifier 113 of voltage transients and interference from nearby electrical equipment and power lines. The gain of the amplifier 113 is determined by the ratio of the value of resistor 137 to that of resistor 133.

Any current which flows through the external patient-glove-surgeon circuit also flows through the belt contact 9 and to ground through resistor 81. The voltage across resistor 81 is applied through resistor 129 to the input 139 of the amplifier 113. The output 141 of the amplifier 113 is applied through resistor 143 to the timing inputs 145 of the timer 115. When the glove resistance 27 is very high and the current through resistor 81 is low (i.e., the glove 1 is providing an effective protective barrier), the output 143 of the amplifier 113 is at or near ground potential, which causes the output 147 of the timer 115 to be held HIGH. When the current through resistor 81 increases as a result of decreasing glove resistance 27 due to liquid saturation, the voltage across resistor 81 and the output 141 of the amplifier 113 increase proportionately. The amplifier output 141 charges capacitor 149 through resistor 143. When the voltage across capacitor 149 reaches the upper threshold voltage of the timer 145, the timer output 147 is switched to LOW and, simultaneously, the timer discharge input 151 connects resistor 153 to ground. Capacitor 149 then discharges through resistor 153. When the voltage across capacitor 149 reaches the timer's lower threshold voltage, the timer output 147 is switched to HIGH and, simultaneously, the timer discharge input 151 is disconnected from ground, which allows the amplifier output 141 to begin charging capacitor 149, beginning the cycle again. Thus, the timer output 147 will switch back and forth between HIGH and LOW. Like the output 91 of the second timer 89 of the continuity circuit 51, the leak detector circuit's timer output 147 controls the alarm indicator 55. Timer output 147 is connected through resistor 148 to the base of transistor 61. When the timer output 147 is LOW, transistor 61 is forward-biased, and +V is applied to the vibrator 59 and alarm LED 15, causing them to vibrate and illuminate, respectively. Assuming that transistor 61 is not forward-biased due to the action of the continuity circuit 51, when the timer output 147 is HIGH, transistor 61 is cut off, and no power is applied to the vibrator 59 and alarm LED 15.

It will be appreciated that if the amplifier output 141 is less than the timer's upper threshold voltage, the timer output 147 will never be switched LOW. When the amplifier output 141 is greater than the timer's upper threshold voltage, the time the timer output 147 is LOW during each HIGH-LOW cycle is essentially constant. However, the time the timer output 147 is HIGH decreases as the amplifier output 141 increases. Thus, as the glove 1 becomes more saturated, the frequency of the timer output 147 increases. In this embodiment, for an amplifier output 141 corresponding to the point at which the glove first begins to saturate (i.e., corresponding to approximately two minutes in FIG. 1), the timer output 147 cycles as follows: LOW for one second, HIGH for five seconds, repeat. As a result, +V is applied to the vibrator 59 and alarm LED 15 for one second, removed for five seconds, then the cycle is repeated. This is the initial imminent failure alarm. As the amplifier output 141 increases, the frequency of the one-second applications of power to the vibrator 59 and alarm LED 15 increases. When the glove 1 is saturated to the extent that it no longer provides an effective barrier to liquid-borne pathogens (corresponding to approximately 3-4 minutes in FIG. 1), the timer output 147 is HIGH for only short periods, which causes the vibrator 59 and alarm LED 15 to operate essentially continuously. This is the glove failure alarm. When a glove 1 is torn or perforated, the amplifier output 141 increases immediately to a voltage in excess of that necessary for a glove failure alarm, thereby causing a glove failure alarm.

The glove failure and imminent glove failure alarms provide valuable information to the surgeon 3. Obviously, a glove failure alarm should prompt the surgeon to take immediate remedial action such as removing the gloves, scrubbing his or her hands, and regloving. An imminent glove failure alarm provides the option of continuing to use his or her present gloves for a brief time, if necessary, with the knowledge that they are still providing an effective protective barrier, but must be changed in a short time.

THE LOW VOLTAGE DETECTION CIRCUIT

When the patient lanyard connector 117 is plugged into the module lanyard connector 119, battery voltage, +V, is monitored by a low voltage monitor circuit 155, such as Motorola, Inc., part number MC34164. +V is connected to the monitor circuit's input 157 and, so long as +V is greater than the circuit's internal reference voltage, the circuit's output 159 is HIGH. When the circuit's output 159 is HIGH, transistor 161 is forward-biased, and capacitor 163 is held at ground potential.

As is the case of the timers 87, 89, discussed in connection with the continuity circuit, the low voltage detection circuit timer 51 operates as an astable multivibrator. When +V drops below the internal reference voltage of the monitoring circuit 155, the circuit's output switches LOW, which cuts off transistor 161, and capacitor 163 is charged through resistor 167 by the HIGH at the timer output 169. As a result, the timer output 169 begins to cycle between HIGH and LOW in the same manner as that described in connection with continuity circuit timers 87, 89. The cycling rate of the timer 165 is determined by the values of capacitor 163 and resistors 163, 167. In this embodiment, the timer output 169 cycles as follows: 0.5 second LOW, two seconds HIGH. When the timer output 169 is LOW, transistor 173 is forward-biased, which applies +V power through resistor 173 to a red low battery LED 174, causing the LED 174 to illuminate. When the timer output 169 switches HIGH, transistor 171 is biased off, V power is removed from LED 174, and the LED 174 extinguishes. Thus, when the voltage of the battery 121 falls below the internal reference voltage of the monitor circuit 155, the battery low LED 174 illuminates 0.5 seconds, extinguishes for two seconds, then repeats the cycle, thereby providing the surgeon a visual indication that the battery voltage is low.

While the low battery detection circuit 57 of this embodiment provides a visual indication of a low battery charge, if desired, the circuit can be easily modified to control the alarm indicator circuit 55 to provide a tactile warning.

The low voltage monitor circuit 155 used in this embodiment was selected because the energy remaining in the battery 121 when its voltage falls below the circuit's internal reference voltage is ample to allow the module 5 to function normally for a reasonable time period, i.e., at least five hours.

TESTING THE SYSTEM

When the test button 33 is pressed, the battery 121 supplies power through resistor 175 to a green test LED 177, causing it to illuminate. Battery power is also applied the module's circuitry through diode 177. Battery power is also applied to resistor 81 through diode 179, causing the leak warning circuit 53 to generate a glove failure alarm, thereby verifying that the leak detector circuit 53 is operable. Battery power is also applied to belt clip 9 and, if both belt clips 7, 9 are not in contact with the surgeon's skin, the continuity circuit 51 generates a continuity alarm. However, since the alarm indicator 55 is also issuing a glove failure alarm (a continuous alarm), the intermittent continuity alarm cannot be discerned. To test the continuity circuit 51, the test button 33 must be released and the patient lanyard contact 117 must be plugged into the module lanyard connector 119. The operability of the continuity circuit 51 can then be checked without the masking effect of the glove failure alarm.

Finally, when the test button 33 is depressed, battery voltage is applied to the low battery warning circuit 57. If the battery voltage is low, the red low battery LED 174 will illuminate. The red low battery LED 175 and the green test LED 177 are combined in the same package. Thus, if the battery voltage is low when the test button 33 is pressed, the combined colors of the test LED 177 and the low battery LED 174 appear amber. To minimize the voltage drop across diode 177, thereby preventing an erroneous low battery warning when the module 5 is tested, diode 177 is a Shottky diode.

The described protective barrier system is quite simple to use. The module's battery 121, leak detection circuit 53, and alarm indicator 55 may be tested at any time by depressing the test button 33. If the battery voltage is sufficient for approximately five hours of normal operation, the status indicator 31 will be green; if not, the status indicator 31 will be amber. While the test button 33 is depressed, the vibrator 59 and red alarm LED 15 will operate continuously, thereby verifying that the leak detector circuit 53 and alarm indicator 55 are operable. The continuity circuit 51 may then be checked by connecting the module lanyard 19 to the patient lanyard 21. If both the belt clips 7, 9 (or both conductive elements of an alternate skin-contact means such as the headband 35) are not in contact with the user's skin, the alarm indicator 55 will indicate a continuity warning; i.e., vibrator 59 and alarm LED 15 on for one second, off for one second, on for one second, off for five seconds, repeat. Placing the belt clips 7, 9 (or both conductive elements of an alternate skin-contacting means such as the headband 35) in contact with the user's skin discontinues the continuity warning.

Summarizing the warnings which may be issued by the module:

1. Conductivity alarm—vibrator 59 and red alarm LED 15 on for one second, off for one second, on for one second, off for five seconds, repeat;
2. Glove failure alarm—vibrator 59 and red alarm LED 15 on continuously; and
3. Imminent glove failure alarm—initially, vibrator 59 and red alarm LED 15 on one second, off five seconds, then on for one second, off for decreasing periods, until they are essentially on continuously.

WIRELESS SYSTEM

Figure 5:
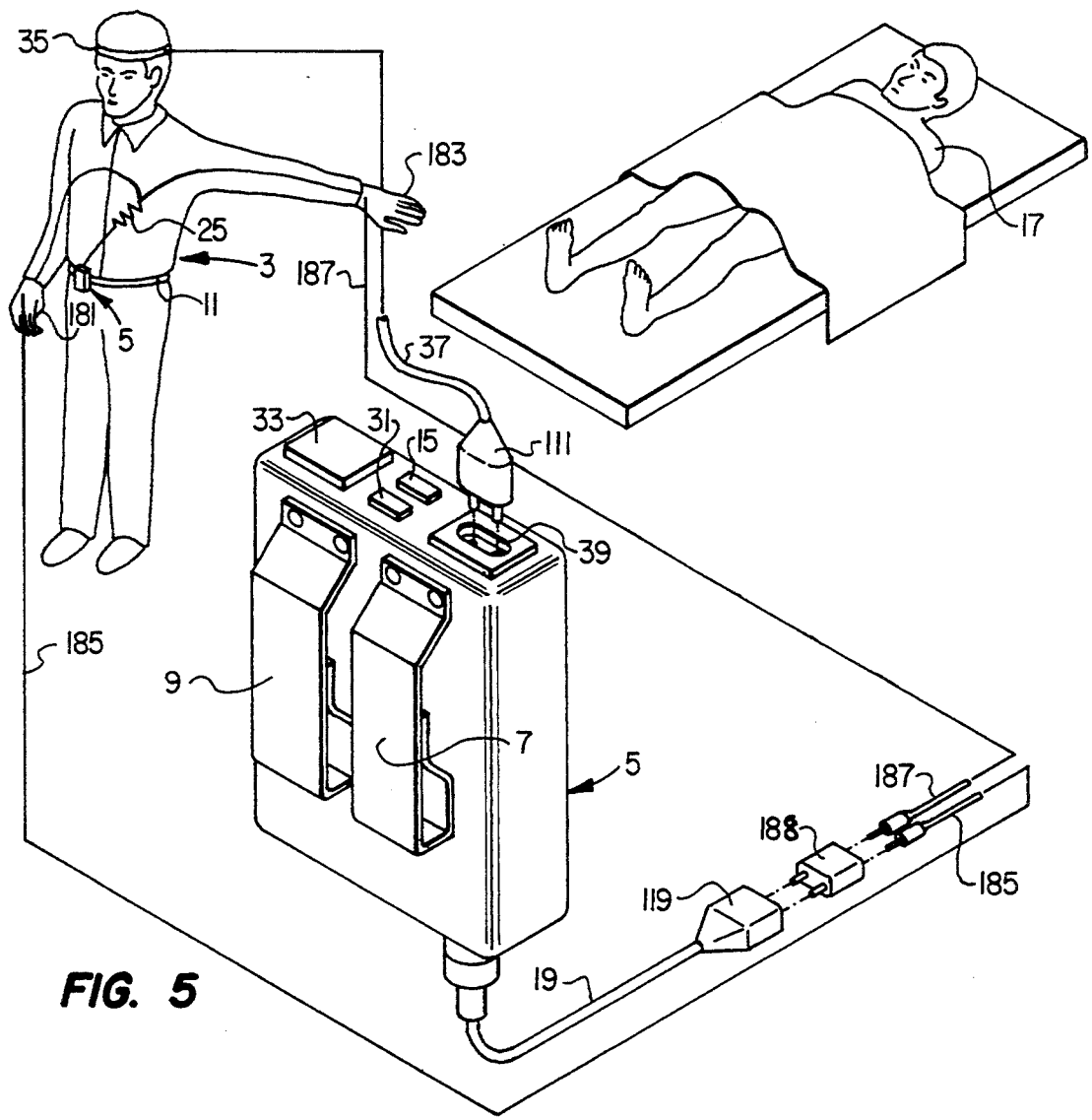
FIG. 5 illustrates an embodiment of the present invention in which no electrical connection between the leak alarm module and the patient is required.
Figure 6:
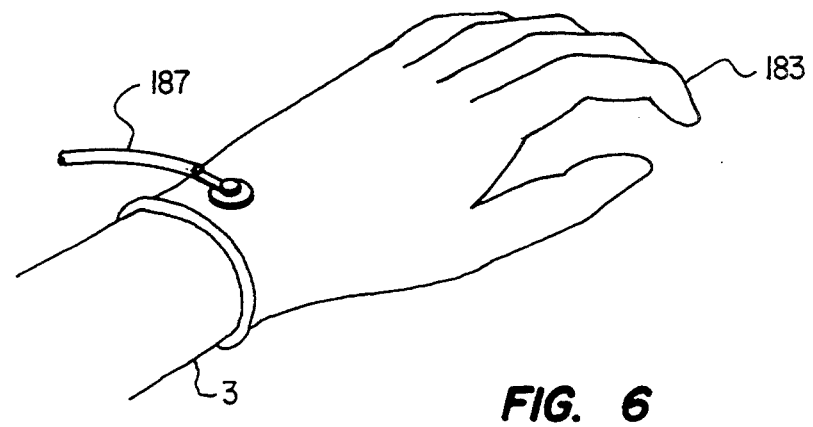
FIG. 6 is an enlarged view of the glove shown in FIG. 5.
Figure 7:
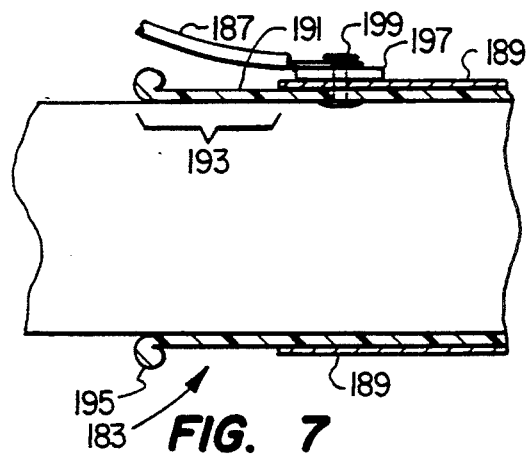
FIG. 7 is a sectional view of the glove shown in FIGS. 5 and 6.

FIGS. 5–7 illustrate an embodiment of the invention in which an electrical connection to the patient 17 is not required. The surgeon's gloves 181, 183 have conductive outer surfaces. Single-conductor glove lanyards 185, 187 are electrically connected to the conductive outer surface of the gloves 181, 183 and to the module lanyard by means of an adapter plug 188.

The gloves 181, 183 are constructed of a conventional material, such as latex. A thin layer 189 of a conductive material, such as carbon, is applied to the outer surface 191 of the glove 183, except for a band 193 at the cuff end 195 of the glove 183. Methods for applying the conductive material to the glove 183, such as by spraying or vapor deposit, are well known and will not be discussed herein. The cuff lanyard 187 is electrically connected to the conductive layer 189 by a contact 197 and mechanically connected to the glove by an nonconductive, rivet-like button 199.

Figure 8:
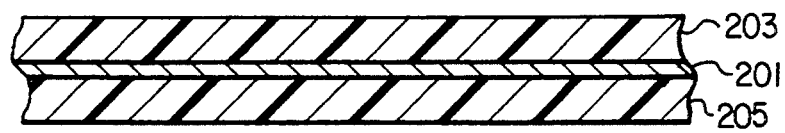
FIG. 8 is a sectional view of a fabric having a conductive layer between outer and inner nonconductive fabric layers.

It will be appreciated that a fabric having a conductive layer may be used to provide a warning of a in the protective barrier provided by the surgeon's clothing. The fabric may be constructed in a manner similar to the gloves 181, 183 described above. Alternately, as shown in cross section in FIG. 8, a conductive layer 201 can be placed between an outer layer 203 and an inner layer 205 of nonconducting fabric. In addition, where additional thickness does not present a problem, the construction shown in FIG. 8 may be used for gloves.

Figure 9:
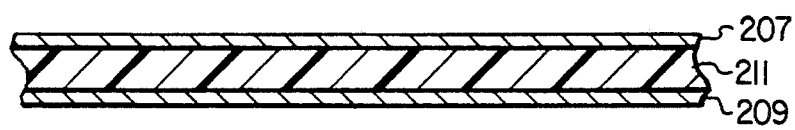
FIG. 9 is a sectional view of a fabric having a nonconductive fabric layer between outer and inner conductive layers.

In many instances, the garment which acts as a protective barrier is worn over other garments, such as when a surgeon wears a surgical gown over his "scrubs." A protective garment constructed of a fabric such as that shown in cross section in FIG. 9 allows the module 5 to provide a warning that the protective barrier has been ed. An outer conductive layer 207 and an inner conductive layer 209 are applied to a center fabric layer 211. The outer conductive layer 207 is electrically connected to the module lanyard 119 (FIG. 4), and the inner conductive layer 209 is electrically connected to the input of the leak detector circuit 53. Obviously, the foregoing connections may be reversed. When a liquid soaks through the outer conductive layer 207 and the fabric layer 211 and contacts the inner conductive layer, a "glove alarm" will be generated.

Figure 10:
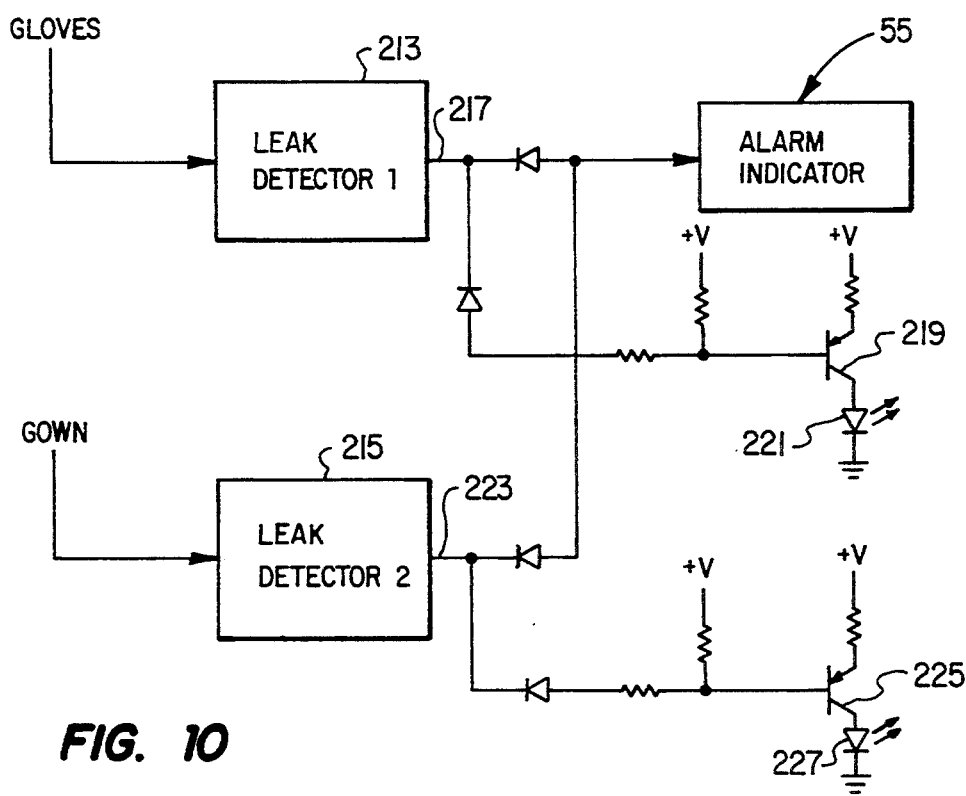
FIG. 10 is a schematic diagram of a modification to the circuitry of FIG. 4 which provides individual visual indications of which of two or more protective barriers has failed.

When two or more protective barriers are connected to the module 5 of the present invention, in any of the barriers causes an alarm. However, the module 5 described in connection with FIG. 4 will not indicate which of the protective barriers has been ed. FIG. 10 shows a modification of the module 5 which provides such an indication. The surgeon's gloves are electrically connected to a glove leak detector 213, and his protective gown is electrically connected to a gown leak detector 215. The glove and gown leak detectors are identical to the leak detector 53 shown in FIG. 4. When, for example, one of the gloves is torn or perforated, the alarm indicator 55 generates a glove leak alarm as described in connection with FIG. 4. Recall that the alarm indicator 55 is actuated when a LOW appears at the output 147 of the leak detector's second timer 115. In this example, the LOW at the glove leak detector's output 217 forward biases transistor 219, illuminating a glove leak LED 221. Similarly, when a "glove failure alarm" is sounded due to a in the protective barrier provided by the surgeon's gown, the LOW at the gown leak detector's output 223 forward biases transistor 225, illuminating a gown leak LED 227. Thus, in addition to knowing that one of his or her protective barriers has been ed, the surgeon can easily determine which barrier has failed.

Figure 11:
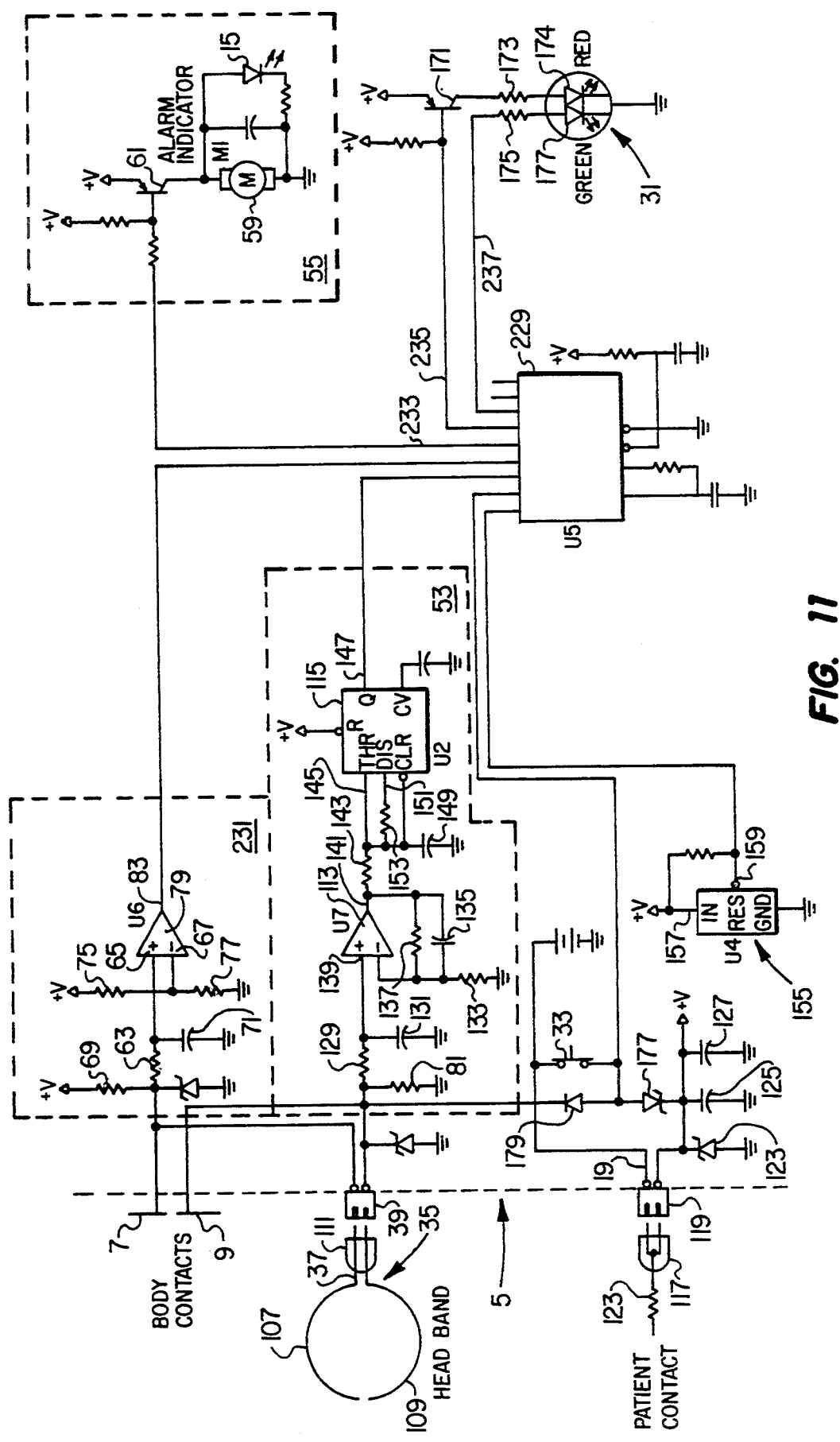
FIG. 11 is a schematic diagram of a microprocessor version of the circuitry of the leak alarm module.

FIG. 11 shows the circuits of an alternate version of the module 5 which includes a single-chip microprocessor 229, such part number MC68HC705K1, manufactured by Motorola, Inc. The microprocessor 229 accepts inputs from a continuity detector circuit 231 (an abbreviated version of the continuity circuit of FIG. 4), the glove leak detector 53, the test button 33, and the low voltage monitor circuit 155. The microprocessor 229 processes those signals in accordance with a program stored in its memory, and provides outputs 233–237 which control the alarm indicator 55 and status indicator 31. A major advantage of this embodiment is that it requires fewer parts, which decreases manufacturing cost. In addition, the microprocessor module in FIG. 11 can be more easily modified than that shown in FIG. 4. To change the level of saturation which generates an imminent glove failure alarm or a glove failure alarm, one merely reprograms the microprocessor. The microprocessor can be programmed to base the imminent glove failure alarm the time derivative of glove resistance. To add additional leak detector circuits, one merely adds the leak detector circuitry and reprograms the microprocessor to sequentially input the detector circuit outputs.

While the embodiments of the present invention described above relate to the medical industry, it will be appreciated that the invention is not limited to that industry. Rather, the invention has broad application. For example, the invention can be applied to the fabric of a space suit, thereby providing the astronaut advance warning that the suit is in danger of failing.

While the preferred embodiment of the invention has been shown and described, it will be apparent to those skilled in this art that various modifications may be made to this embodiment without departing from the spirit of the present invention. For that reason, the scope of the invention is set forth in the following claims.

I claim:

1. An apparatus for monitoring the integrity of a personal protective barrier worn by a worker comprising:

a detection circuit electrically connected to first and second contacts and operable to sense the electrical resistance between said first and second contacts;

said first contact being electrically connected to said worker and said second contact being electrically connected to an external object, said worker, said protective barrier, and said external object being included in an electrical circuit between said first and second contacts;

said detection circuit being electrically connected to an alarm and, only when the electrical resistance between said first and second contacts is below a predetermined level, said detection circuit being operable to provide a variable signal to activate said alarm, said variable signal comprising a periodic signal, the frequency of which increases as said resistance decreases.

2. The apparatus of claim 1 wherein, when the resistance sensed by said detection circuit is below a second predetermined value, said variable signal comprises a substantially continuous signal.

3. The apparatus of claim 6 further comprising:

a continuity circuit electrically connected to said first contact, and to a third contact and operable to sense the electrical resistance between said first and third contacts;

said first contact and said third contact being electrically connected to spaced apart locations on said worker; and said continuity circuit being electrically connected to said alarm and operable to provide a signal to activate said alarm when the electrical resistance sensed by said continuity circuit is greater than a second predetermined value, the signal provided by the continuity circuit comprising a signal having at least one characteristic which differs from a corresponding characteristic of the variable signal provided by said detector circuit;

whereby, an alarm resulting from activation by the signal provided by said continuity circuit is substantially distinguishable by said worker from an alarm resulting from activation by the variable signal provided by said detection circuit.

* * * * *